(12) United States Patent
Blanski

(10) Patent No.: US 9,266,914 B2
(45) Date of Patent: Feb. 23, 2016

(54) BACKFLUORINATED NHC CARBENES AND COMPLEXES

(71) Applicant: The United States of America, as Represented by the Secretary of the Air Force, Washington, DC (US)

(72) Inventor: Rusty Lew Blanski, Palmdale, CA (US)

(73) Assignee: The United States of America, as requested by the Secretary of the Air Force, Washington, DC (US)

( * ) Notice: Subject to any disclaimer, the term of this patent is extended or adjusted under 35 U.S.C. 154(b) by 179 days.

(21) Appl. No.: 13/927,295

(22) Filed: Jun. 26, 2013

(65) Prior Publication Data

US 2015/0004322 A1  Jan. 1, 2015

(51) Int. Cl.
  *C07F 15/00* (2006.01)
  *C23C 16/18* (2006.01)
  *C07D 233/02* (2006.01)
  *C07D 233/22* (2006.01)
  *C23C 18/16* (2006.01)
  *C23C 18/44* (2006.01)

(52) U.S. Cl.
  CPC .......... *C07F 15/0033* (2013.01); *C07D 233/02* (2013.01); *C07D 233/22* (2013.01); *C23C 18/1635* (2013.01); *C23C 18/1658* (2013.01); *C23C 18/1678* (2013.01); *C23C 18/1685* (2013.01); *C23C 18/1692* (2013.01); *C23C 18/44* (2013.01)

(58) Field of Classification Search
  CPC .. C07D 233/02; C07D 233/22; C07F 15/0033
  See application file for complete search history.

(56) References Cited

U.S. PATENT DOCUMENTS

| 5,789,027 A | 8/1998 | Watkins et al. |
| 7,622,590 B1 | 11/2009 | Nolan et al. |
| 7,902,389 B2 | 3/2011 | Nolan et al. |
| 2011/0087032 A1 | 4/2011 | Kuhn et al. |

OTHER PUBLICATIONS

Khramov et al. "N-Heterocyclic carbenes: deducing sigma- and pi-contributions in Rh-catalyzed hydroboration and Pd-catalyzed coupling reactions" Tetrahedron, 2008, vol. 64, pp. 6853-6862.*
C. F Karanikas, "Supercritical fluid deposition of thin metal films: kinetics, mechanics and applications," Dissertation Submitted to the Graduate School of the University of Massachusetts. (2009) 230 pages total.
D. M. Khramov et al., "N-heterocyclic carbenes: deciding σ- and π-contributions in Rh-catalyzed hydroboration and Pd-catalyzed coupling reactions, "Tetrahedron, vol. 64 (2008) 6853-6862.
M. G. Hobbs et al., "The influence of electrn delocation upon the stability and structure of potential N-heterocyclic carbene precursors with 1,3-diaryl-imidazolidine-4,5-dione skeletons," New J. Chem., vol. 34 (2010) 1295-1308.
A. G. Tennyson et al., "Arrest catalysis: controlling kumada coupling activity via a redox-active n-heterocyclic carbene," JACS, vol. 132 (2010) 9420-9429.
D. M. Khramov et al., "N-heterocyclic carbene—transition metal complexes: spectroscopic and crystallographic analysis of π-backbonding interactions," Organomet., vol. 26 (2007) 6042-6049.
X-R Ye, "Supercritical fluid fabrication of metal nanowires and nanorods templated by multiwalled carbon nanotubes," Adv. Mater., vol. 15 (2003) 316-319.
O. Aschenbrenner et al., "Solubility of B-diketonates, cyclopentadienyls, and cyclooctadiene complexes with various metals in supercritical carbon dioxide," J. Supercrit. Fluids, vol. 41 (2007) 179-186.
J. M. Blackburn et al., "Deposition of conformal copper and nickel films from supercritical carbon dioxide," Science, vol. 294 (2001) 141-145.
A. Cabanas et al., "Deposition of Cu films from supercritical fluids using Cu(I) B-diketonate precursors," Microelec. Eng., vol. 64 (2002) 53-61.
C. F. Karanikas et al., "Kinetics of the ruthenium thin film deposition from supercritical carbon dioxide by the hydrogen reduction of Ru(tmhd)2cod," Microelect. Eng., vol. 87 (2010) 566-572.
J. W. Sprengers, "Palladium-(N-heterocyclic carbene) hydrogenation catalysts," Angew. Chem. Int. Ed., vol. 44 (2005) 2026-2029.
S. Diez-Gonzalez et al, "N-heterocylic carbenes in late transition metal catalysis," Chem. Rev., vol. 109 (2009) 3612-3676.

(Continued)

*Primary Examiner* — Joseph Kosack
(74) *Attorney, Agent, or Firm* — AFMCLO/JAZ; Chastity Whitaker

(57) ABSTRACT

N-heterocyclic ("NHC") carbenes and NHC carbene-metal complexes. The NHC carbene having a formula:

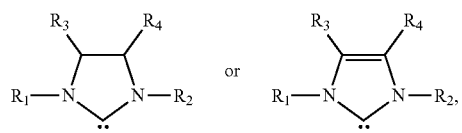

wherein $R_1$ is an aromatic or aliphatic group, and $R_2$ is an aromatic or aliphatic group, $R_3$ is a fluorinated alkyl chain, $R_4$ is a fluorinated alkyl chain or a proton. NHC carbene-metal complexes having the formula:

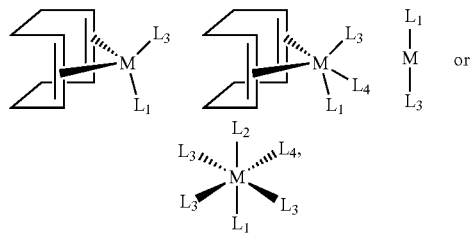

wherein M is a metal, and each of $L_1$, $L_2$, and $L_3$ ligands is a backfluorinated NHC carbene.

18 Claims, 13 Drawing Sheets

(56) References Cited

OTHER PUBLICATIONS

R. H. Crabtree et al., "Cationic iridium diolefin complexes as alkene hydrogenation catalysts and the isolation of some related hydrido complexes," J. Organomet. Chem., vol. 141 (1977) 205-215.

M. T. Powell et al., "Chiral imidazolylidine ligands for asymmetric hydrogenation of aryl alkenes," J. Am. Chem. Soc., vol. 123 (2001) 8878-8879.

H. M. Lee et al., "A cationic iridium complex bearing an imidazol-2-ylidene ligand as alkene hydrogenation catalyst," Organomet., vol. 20 (2001) 1255-1258.

J. A. Darr et al., "New directions in inorganic and metal-organic coordination chemistry in supercritical fluids," Chem. Rev., vol. 99 (1999) 495-541.

L. Xu et al., "Fluoroalkylated N-heterocyclic carbene complexes of palladium," J. Organomet. Chem., vol. 598 (2000) 409-416.

M. G. Hobbs et al., "Anionic N-heterocyclic carbenes with N,N'-bis(fluoroaryl) and N,N'-bis(perfluoroaryl) substituents," Chem. Eur. J., vol. 16 (2010) 14520-14533.

J. W. Ogle et al., "Synthesis of electronically diverse tetraarylimidazolyidene carbenes via catalytic aldimine coupling," Org. Lett., vol. 10 (2008) 3677-3680.

T. Ritter et al., "Rate acceleration in olefin metathesis through a fluorine-ruthenium interaction," JACS Comm., vol. 128 (2006) 11768-11769.

M. Skalicky et al., "Synthesis of bis(polyfluoroalkylated)imidazolium salts as key intermediates for fluorous NHC ligands," J. Fluorine Chem., vol. 130 (2009) 966-973.

S. McGrandle et al., "Group 9 complexes of an N-heterocycle carbene bearing a pentafluorobenzyl substituent: attempted dehydrofluorinative coupling of cyclopentadienyl and N-heterocycle carbene ligands," J. Fluorine Chem., vol. 126 (2005) 451-455.

S. Burling et al., "Neutral and cationic fluorinated N-heterocyclic carbene complexes of rhodium and iridium," Organomet., vol. 25 (2006) 3761-3767.

I. T. Horvath et al., "Facile catalyst seperation without water: fluorous biphase hydroformylation of olefins," Science., vol. 266 (1994) 72-75.

I. T. Horvath et al., "Fluoros biphase chemistry," ACC Chem. Res., vol. 31 (1998) 641-650.

R. C. Da Costa et al., "Syntheses and reactivity of analogoes of Grubbs' second generation metathesis catalyst with fluorous phosphines: a new phase-transfer strategy for catalyst activation," Adv. Synth. Catal., vol. 349 (2007) 243-254.

Q. Yao et al, "Syntheses and reactivity of analogoes of Grubbs' second generation metathesis catalyst with fluorous phosphines: a new phase-transfer strategy for catalyst activation," JACS Comm., vol. 126 (2004) 74-75.

M-S. Weiser et al., "Cobalt(II) octanoate and colbalt(II) perfluorooctanoate catalyzed atom transfer radical polymerization of styrene in toluene and fluorous media—a versatile route to catalyst recycling and oligomer formation," J. Poly. Sci. Part A: Poly. Chem., vol. 43 (2005) 3804-3813.

* cited by examiner

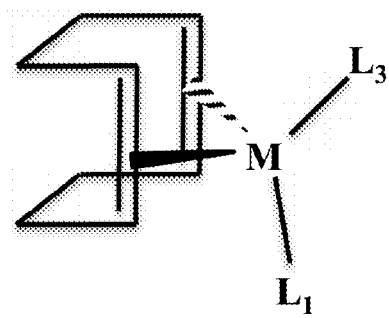
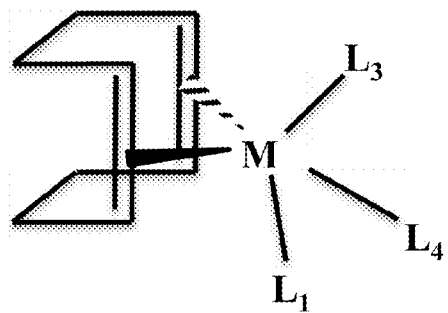
FIG. 5A  FIG. 5B
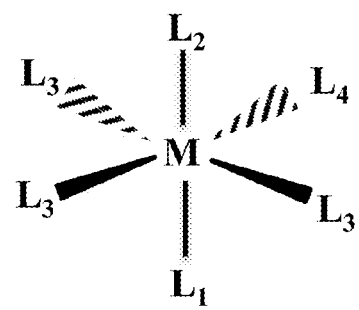
FIG. 5C  FIG. 5D

BACKFLUORINATED NHC CARBENES AND COMPLEXES

RIGHTS OF THE GOVERNMENT

The invention described herein may be manufactured and used by or for the Government of the United States for all governmental purposes without the payment of any royalty.

FIELD OF THE INVENTION

The present invention related generally to supercritical fluid deposition and, more particularly, to methods of depositing metals using cold wall reactor supercritical fluid deposition procedures.

BACKGROUND OF THE INVENTION

Chemical vapor deposition (hereafter, "CVD") is a conventionally used process for producing high-purity, high-performance materials, such as thin films on semiconductors or growing crystalline structures. Deposition of the films includes exposing a substrate to volatile chemicals, i.e., precursors, which react and/or decompose at a surface of the substrate.

The use of CVD for metal deposition, e.g., organometallic CVD or MOCVD, includes a metal atom (for example, but not limited to, Mo, Ta, Ti, W, Ru, Cu, Pt, and Pd) bonded to organic ligands. However, the CVD process has limitations in that internal structures or surfaces, with tortuous features, are not effectively coated.

Supercritical chemical fluid deposition (hereafter, "SFD") is one conventional solution that is capable of depositing a metal coating onto a complicated surface/feature structure. During a SFD process, a supercritical fluid (substances at a temperature and pressure above a critical point (in a phase diagram) such that distinct gas and liquid phases do not exist), also referred to as the working fluid, is used as a solvent to the organometallic precursor. There are many supercritical fluids available for SFD process, but the most convenient may be carbon dioxide. The liquid-like state of the supercritical fluid enables increased solubility of the organometallic precursor, and the gas-like state of the supercritical fluid enables a deep, conformal penetration of the features of the substrate.

SFD processes have conventionally been performed in a hot-wall processing system 10, an example of which is shown in FIG. 1. The hot-wall processing system 10 includes a processing chamber 12 enclosing a processing space 14 that is heated externally. A substrate 16 and an organometallic precursor 18 are added to the processing chamber 12 and sealed. A working fluid (represented by arrows 20) is added, for example, via an injection system 22, and the processing space 14 and heated until the temperature and pressure required for the supercritical state of the working fluid is exceeded. The organometallic precursor 18 dissolves in the supercritical working fluid within the process space 14. A reducing agent, usually hydrogen, is then introduced to cause the metal portion of the organometallic precursor 18 to deposit onto the substrate 16. However, the metal portion is also deposited on other, interior surfaces of the processing chamber 12.

While the hot-wall processing system 10 of FIG. 1 is effective at coating substrates 16, the process is wasteful in that it deposits metal on all surfaces within the processing chamber 12. An alternative to the hot-wall processing system 10 is a cold-wall processing system 30, which is shown in shown in FIG. 2. The cold-wall processing system 30 places a substrate 32 on a heated pedestal 34 within the processing space 36 of the processing chamber 38. With the substrate 32 and an organometallic precursor 40 in place, the processing chamber 38 is sealed and evacuated. A working fluid (represented by arrows 42) is added, for example, via an injection system 44, and the processing chamber 38 is heated until the supercritical state of the working fluid is surpassed. The organometallic precursor 40 dissolves in the supercritical working fluid, and then the reducing agent (again, usually hydrogen) is added. To prevent deposition of the metal component onto all interior surfaces of the chamber 38 (like the aforementioned hot-wall processing system 10 (FIG. 1)), the organometallic precursor 40 should be thermally stable, stable to hydrogen reduction at lower temperature, and yet able to be reduced at elevated temperatures. The pedestal 34 of the cold-wall processing system 30 is heated such that deposition of the metallic portion is on the substrate and pedestal. Thus, the cold-wall processing system is more efficient than the hot-wall process 10 (FIG. 1), and is particularly useful for depositing copper and ruthenium coatings.

However, the cold-wall processing system 30 has not been conventionally used to deposit noble metals because conventional noble metal precursors were not stable under cold-wall SFD processing conditions. As such, there remains a need for noble metal precursors that would undergo SFD using a cold-wall processing system.

SUMMARY OF THE INVENTION

The present invention overcomes the foregoing problems and other shortcomings, drawbacks, and challenges of depositing noble metals using a cold wall supercritical fluid deposition processes. While the invention will be described in connection with certain embodiments, it will be understood that the invention is not limited to these embodiments. To the contrary, this invention includes all alternatives, modifications, and equivalents as may be included within the spirit and scope of the present invention.

According to one embodiment of the present invention, a N-heterocyclic ("NHC") carbene has a formula:

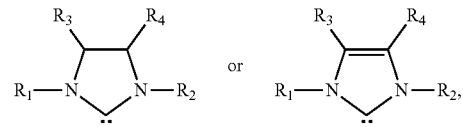

wherein $R_1$ is an aromatic or aliphatic group, and $R_2$ is an aromatic or aliphatic group, $R_3$ is a fluorinated alkyl chain, $R_4$ is a fluorinated alkyl chain or a proton.

According to one aspect of the present invention, the backfluorinated NHC carbene has a formula:

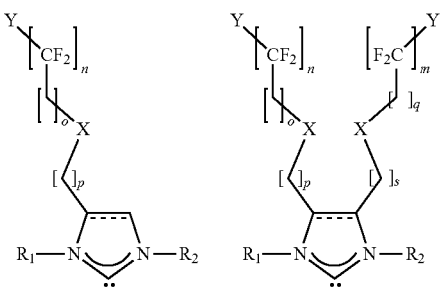

-continued

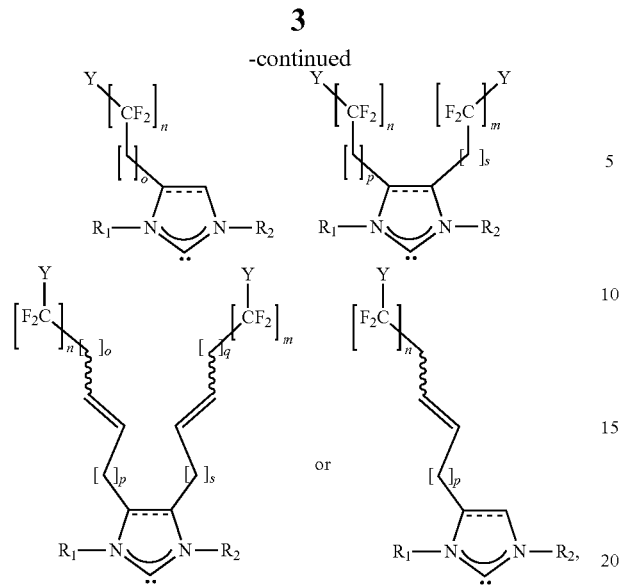

wherein X is oxygen, sulfur, nitrogen monohydride, or $SiR_2^1$ of which $R^1$ is an alkyl or an aryl; Y is hydrogen, fluorine, an aromatic ring, or combinations thereof; and each of $R_1$ and $R_2$ is separately selected from a group consisting of hydrogen, a $C_1$-$C_{20}$ alkyl, a $C_2$-$C_{20}$ alkenyl, a $C_2$-$C_{20}$ alkynyl, a $C_2$-$C_{20}$ alkoxycarbonyl, a $C_1$-$C_{20}$ carboxylate, a $C_1$-$C_{20}$ alkoxy, a $C_2$-$C_{20}$ alkenyloxy, a $C_2$-$C_{20}$ alkynyloxy, an aryl, or an aryloxy. The subscript m may range from 2 to 20, the subscript n may range from 2 to 20, the subscript o may range from 0 to 3, the subscript p may range from 0 to 3, the subscript q may range from 0 to 3, and the subscript s may range from 0 to 3, wherein o+p+q+s>1.

Still another embodiment of the present invention is directed to an NHC carbene-metal complex having a formula:

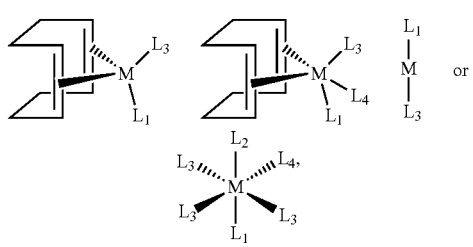

wherein M is a metal, and at least one of the $L_1$, $L_2$, $L_3$, and $L_4$ ligands is a backfluorinated NHC carbene, or a combination of a backfluorinated NHC carbene and acetylacetonate, alkoxy, alkyl, aryl, aryloxy, carbonyl, halide, imido, oxo, pyridine, trialkylphosphine, or triarylphosphine.

Still another embodiment of the present invention is directed to a method of depositing a noble metal onto a substrate using a supercritical fluid deposition process in a cold wall reactor. The method includes exposing the substrate to a supercritical solvent in a supercritical state. The NHC carbene-metal complex, of which M is the noble metal, is dissolved into the supercritical working fluid and a reducing agent is injected. The substrate is heated such that the NHC carbene to be deposited onto the substrate.

In accordance with another embodiment of the present invention, a metal complex having a formula:

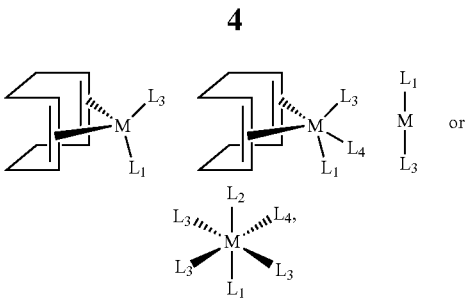

M is a metal, and at least one of $L_1$, $L_2$, $L_3$, and $L_4$ ligands is a backfluorinated NHC carbene.

According to one aspect of the present invention, the backfluorinated NHC carbene of the at least one of the $L_1$, $L_2$, $L_3$, and $L_4$ ligands has a formula:

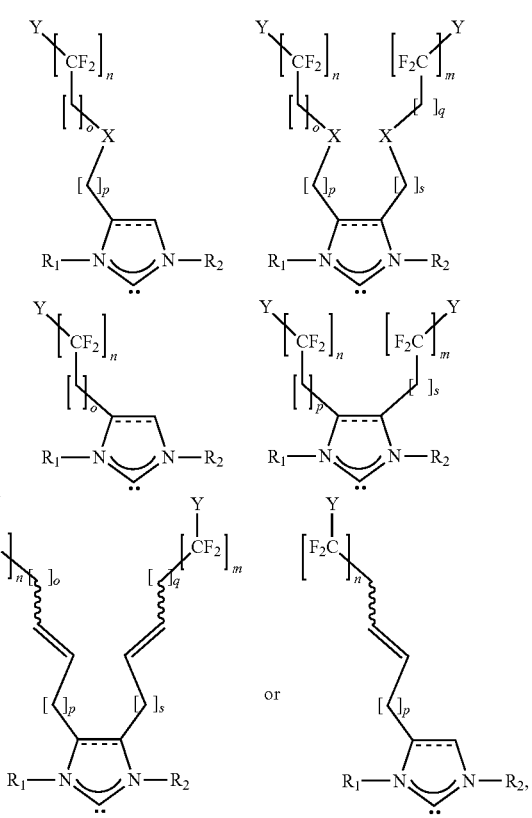

wherein X is oxygen, sulfur, nitrogen monohydride, or $SiR_2^1$ of which $R^1$ is an alkyl or an aryl; Y is hydrogen, fluorine, an aromatic ring, or combinations thereof; and each of $R_1$ and $R_2$ is separately selected from a group consisting of hydrogen, a $C_1$-$C_{20}$ alkyl, a $C_2$-$C_{20}$ alkenyl, a $C_2$-$C_{20}$ alkynyl, a $C_2$-$C_{20}$ alkoxycarbonyl, a $C_1$-$C_{20}$ carboxylate, a $C_1$-$C_{20}$ alkoxy, a $C_2$-$C_{20}$ alkenyloxy, a $C_2$-$C_{20}$ alkynyloxy, an aryl, or an aryloxy. The subscript m may range from 2 to 20, the subscript n may range from 2 to 20, the subscript o may range from 0 to 3, the subscript p may range from 0 to 3, the subscript q may range from 0 to 3, and the subscript s may range from 0 to 3, wherein o+p+q+s>1.

According to one aspect of the present invention, the backfluorinated NHC carbene of the at least one of the $L_1$, $L_2$, $L_3$, and $L_4$ ligands has a formula:

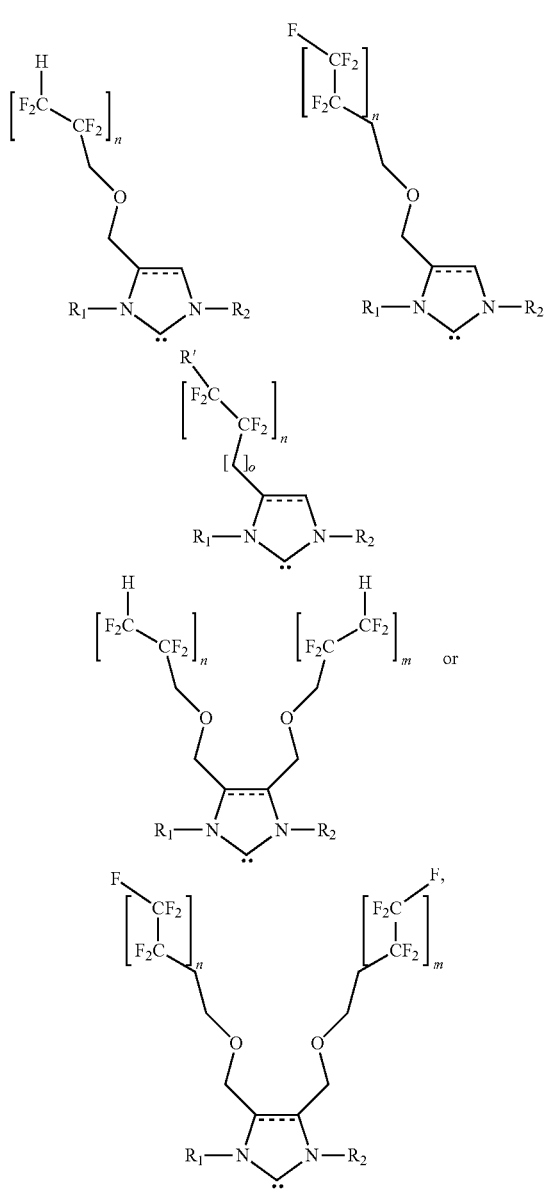

wherein R', when present, is hydrogen, fluorine, an aromatic ring, or combinations thereof and each of $R_1$ and $R_2$ is a hydrogen, a $C_1$-$C_{20}$ alkyl, a $C_2$-$C_{20}$ alkenyl, a $C_2$-$C_{20}$ alkynyl, a $C_2$-$C_{20}$ alkoxycarbonyl, a $C_1$-$C_{20}$ carboxylate, a $C_1$-$C_{20}$ alkoxy, a $C_2$-$C_{20}$ alkenyloxy, a $C_2$-$C_{20}$ alkynyloxy, an aryl, or an aryloxy. The subscript m may range from 1 to 10, the subscript n may range from 1 to 10, and the subscript o may range from 0 to 3.

Additional objects, advantages, and novel features of the invention will be set forth in part in the description which follows, and in part will become apparent to those skilled in the art upon examination of the following or may be leaned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

FIGS. 5A-5D are schematic representations of backfluorinated N-heterocyclic carbene-metal complexes, generalized to include cyclooctadiene and other ligands, according to other embodiments of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Figure 3A:
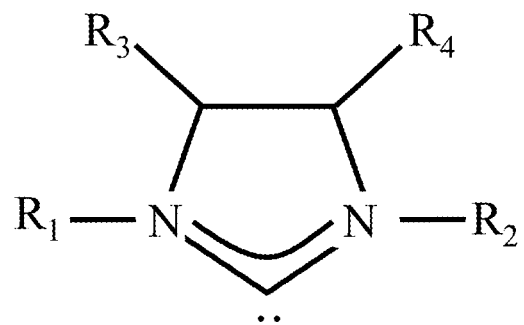
FIGS. 3A and 3B are schematic representations of N-heterocyclic carbenes according to two embodiments of the present invention.
Figure 3B:
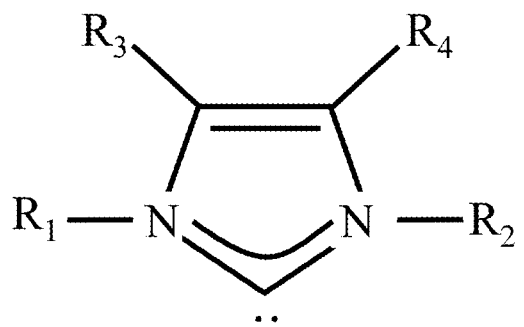
Figure 4A:
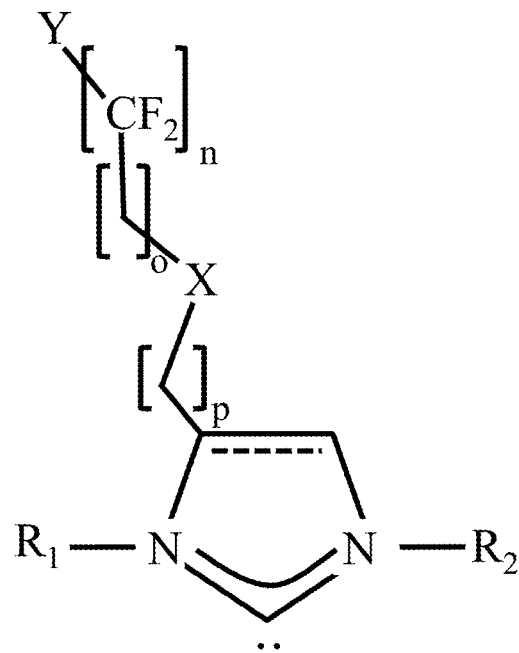
FIGS. 4A-4F are schematic representations of backfluorinated N-heterocyclic carbenes according to various embodiments of the present invention.
Figure 4B:
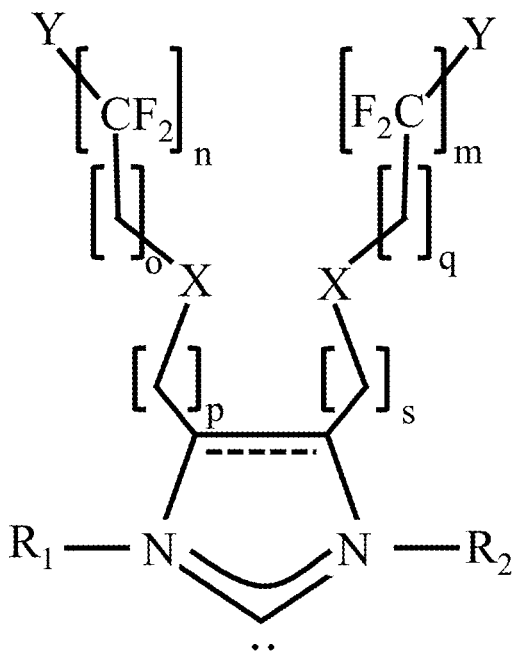
Figure 4C:
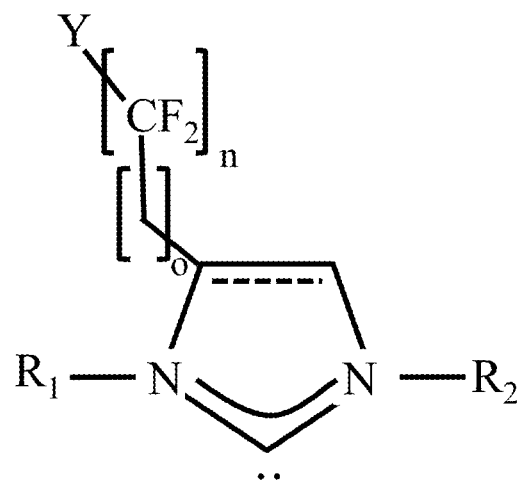
Figure 4D:
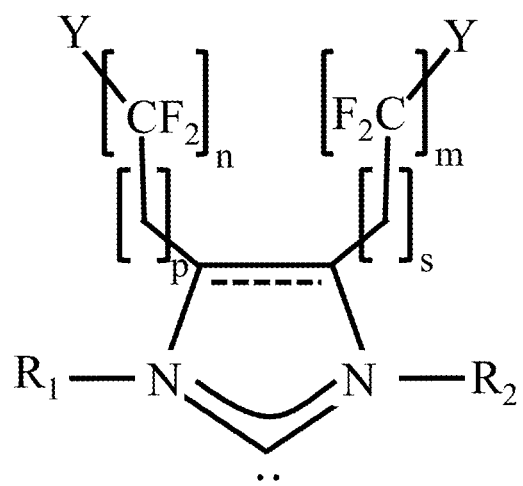
Figure 4E:
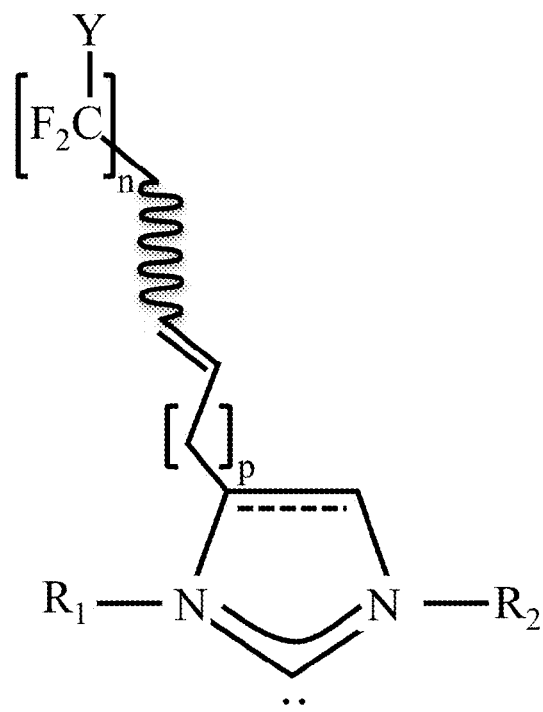
Figure 4F:
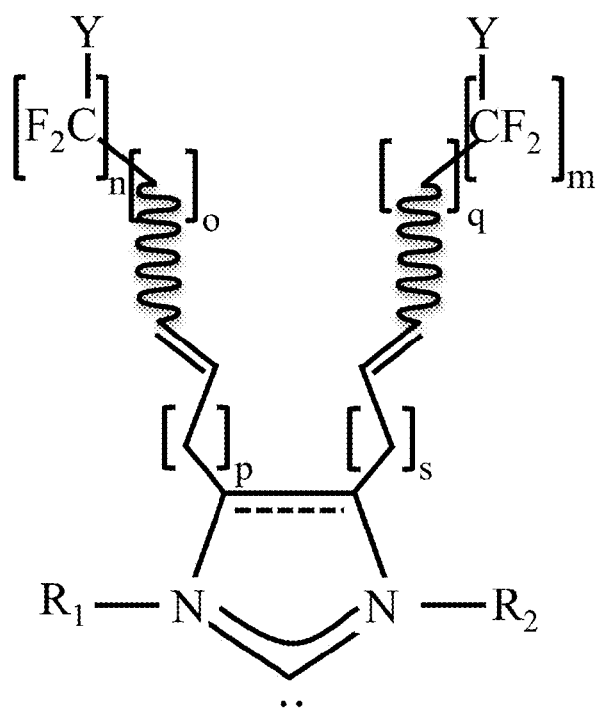

Turning now to the figures, and in particular to FIGS. 3A and 3B an N-heterocyclic ("NHC") carbene according to embodiments of the present are shown generally and wherein, $R_1$ is an aromatic or aliphatic group, and $R_2$ is an aromatic or aliphatic group, $R_3$ is a fluorinated alkyl chain, $R_4$ is a fluorinated alkyl chain or a proton.

With reference now to FIGS. 4A-4F, backfluorinated N-heterocyclic ("NHC") carbene according to other embodiments of the present invention are shown and include full or partial fluorination of an alkyl chain, an alkoxy chain, an alkenyl chain, or a combination thereof on a back of the NHC carbene (hereafter referenced as a "backfluorinated NHC carbenes"). For the backfluorinated NHC carbenes of FIGS. 4A-4F, X is oxygen, sulfur, nitrogen monohydride, or $SiR_2^1$ of which $R^1$ is an alkyl or an aryl; Y is hydrogen, fluorine, an aromatic ring, or combinations thereof; and each of $R_1$ and $R_2$ is separately selected from a group consisting of hydrogen, a $C_1$-$C_{20}$ alkyl, a $C_2$-$C_{20}$ alkenyl, a $C_2$-$C_{20}$ alkynyl, a $C_2$-$C_{20}$ alkoxycarbonyl, a $C_1$-$C_{20}$ carboxylate, a $C_1$-$C_{20}$ alkoxy, a $C_2$-$C_{20}$ alkenyloxy, a $C_2$-$C_{20}$ alkynyloxy, an aryl, or an aryloxy. The subscript m may range from 2 to 20, the subscript n may range from 2 to 20, the subscript o may range from 0 to 3, the subscript p may range from 0 to 3, the subscript q may range from 0 to 3, and the subscript s may range from 0 to 3, wherein o+p+q+s>1. If desired, $R_1$ and $R_2$ may further be substituted with fluorinated or partially fluorinated aromatic group, $C_1$-$C_5$ alkyl, $C_1$-$C_5$ alkoxy, $C_1$-$C_{20}$ alkyl, $C_1$-$C_{20}$ alkoxy, and a halogen substituted phenyl group.

The backfluorinated NHC carbene, as first and second ligands, $L_1$ and $L_2$, may be attached to a metal center, with additional ligands, to yield a backfluorinated NHC carbene-metal complex, as shown in FIGS. 5A-5D. Selection of the metal may depend on a particular application or use of the inorganic backfluorinated NHC carbene-metal complex. For example, in supercritical fluid deposition, M may be selected from the group consisting of rhenium, ruthenium, osmium, rhodium, iridium, palladium, platinum, silver, and gold; in catalysis processes, M may be selected from the group consisting of rhenium, ruthenium, osmium, cobalt, rhodium, iridium, nickel, palladium, platinum, copper, silver, and gold.

A third ligand, $L_3$, as shown in FIGS. 5A-5D, may be selected from the group consisting of an acetylacetonate, alkoxy, alkyl, aryl, aryloxy, carbonyl, halide, imido, oxo, pyridine, trialkylphosphine, or triarylphosphine; and a fourth ligand, $L_4$, may be selected from the group consisting of the group of molecules illustrated in FIGS. 4A-4F, an acetylacetonate, alkoxy, alkyl, aryl, aryloxy, carbonyl, halide, imido, oxo, pyridine, trialkylphosphine, or triarylphosphine. The metal of FIG. 5A may be selected from the group consisting of cobalt, iridium, and rhodium; the metal of FIG. 5B may be selected from the group consisting of nickel, palladium, and platinum; the metal of FIG. 5C may be selected from the group consisting of copper, silver, and gold; and the metal of FIG. 5D may be selected from the group consisting of rhenium, ruthenium, osmium, cobalt, rhodium, iridium, nickel, palladium, and platinum.

Figure 6A:
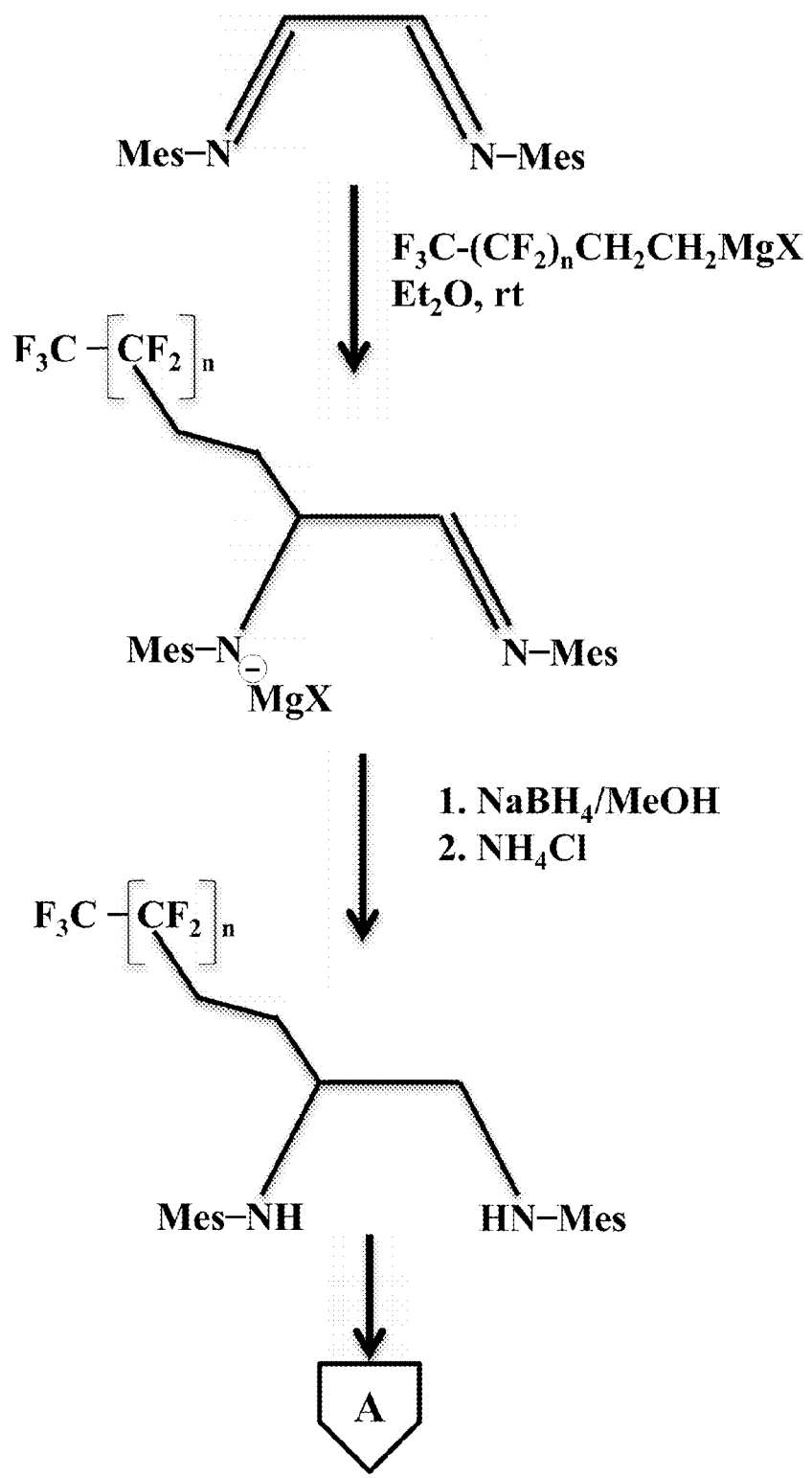
FIGS. 6A-6C are schematic representations of a mechanism for synthesizing backfluorinated NHC carbene metal complexes with aromatic functionality according to one embodiment of the present invention.
Figure 6B:
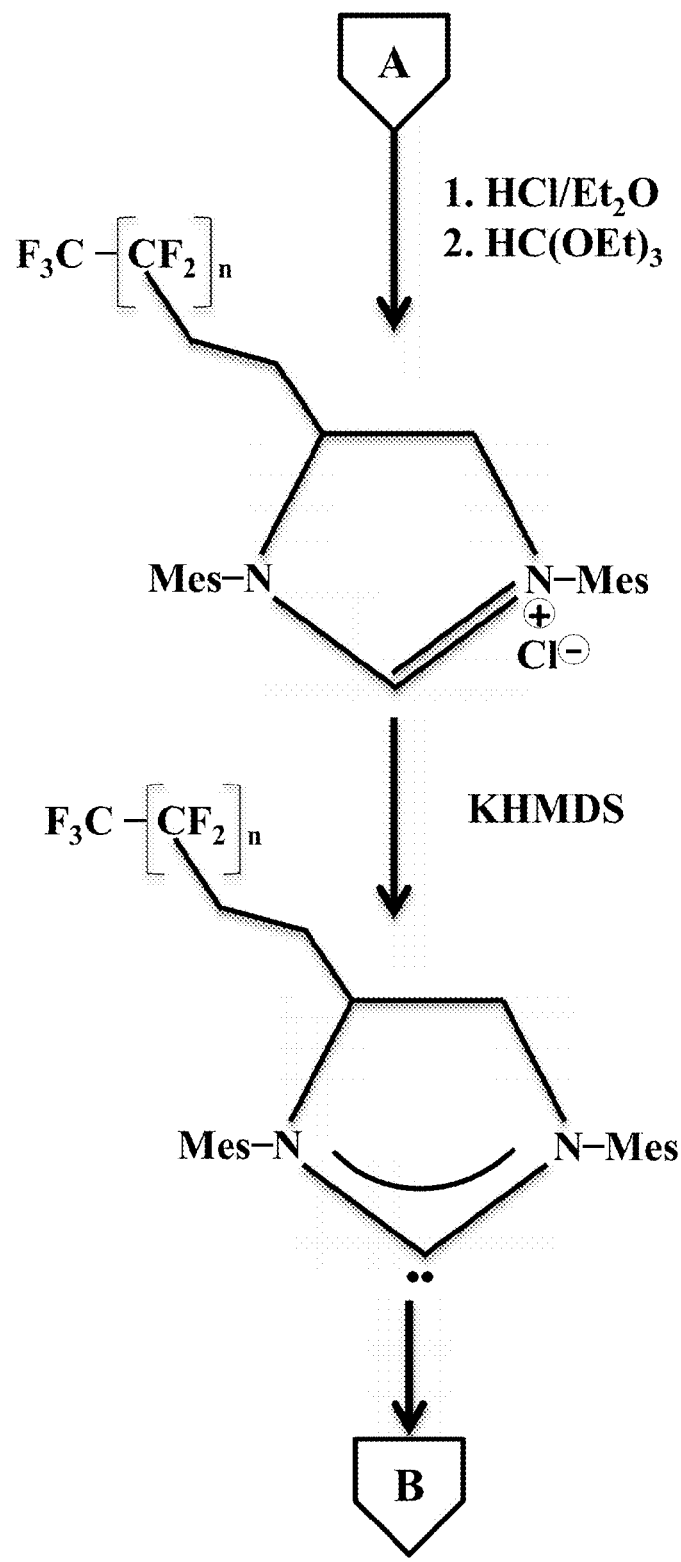
Figure 6C:
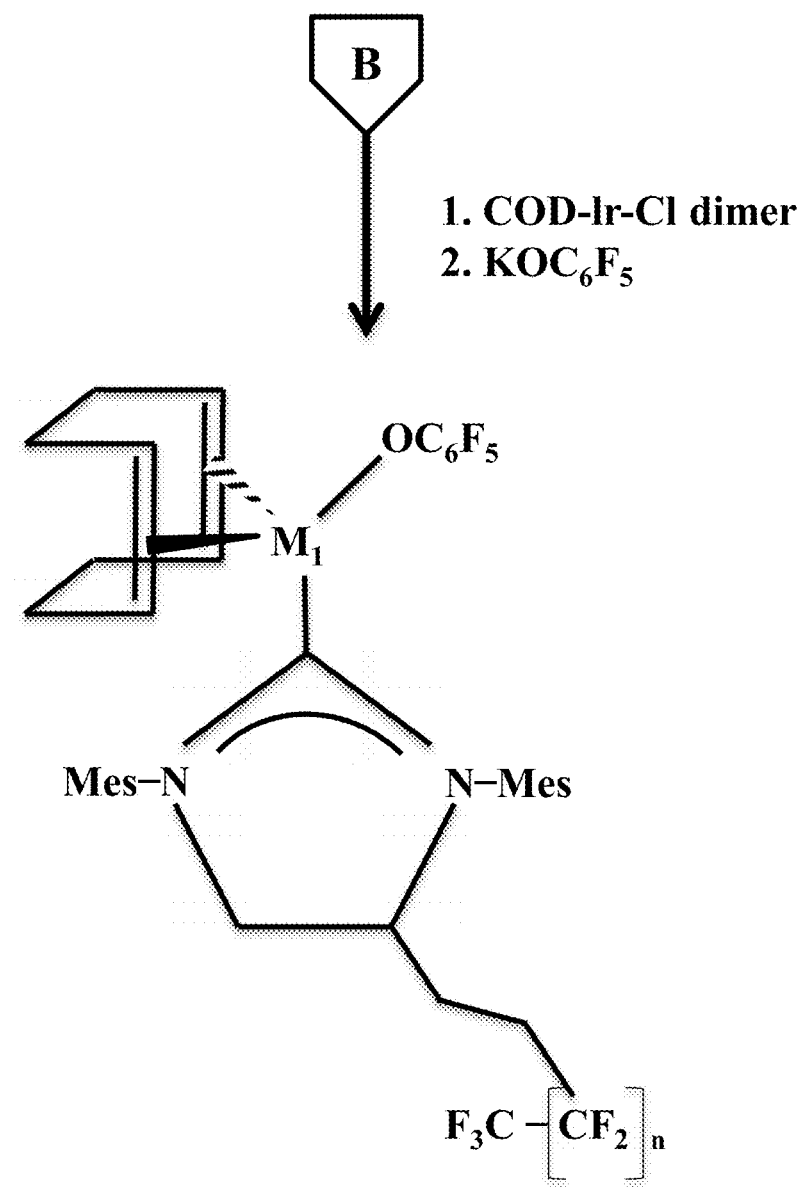

With reference now to FIGS. 6A-6C, a mechanism for synthesizing a backfluorinated NHC carbenes with aromatic functionality according to one embodiment of the present invention is described in detail. In FIG. 6A, mesityl diimine (mesityl group is illustrated as "Mes"), is drop-wise treated with a solution of perfluorohexyl(ethyl)magnesium iodide. Sodium borohydride reduces the remaining imine functionality, and ammonium chloride neutralizes the formed base. A first precursor may be isolated via ether extraction.

In FIG. 6B, hydrogen chloride may be added to the extract, in ether, to precipitate the hydrogen chloride salt. The hydrogen chloride salt is isolated, washed, dried under vacuum, and added to triethyl orthoformate. The solution is heated overnight and then cooled to form the product. The product may be isolated, washed, and dried to afford a white solid. Potassium bis(trimethylsilyl)amide ("KHMDS"), or other sufficiently strong base, may be added to form the carbene, which may, in turn and as illustrated herein, be added to a chlorocyclooctadiene-iridium dimer, the latter of which is shown in FIG. 6C.

Figure 7:
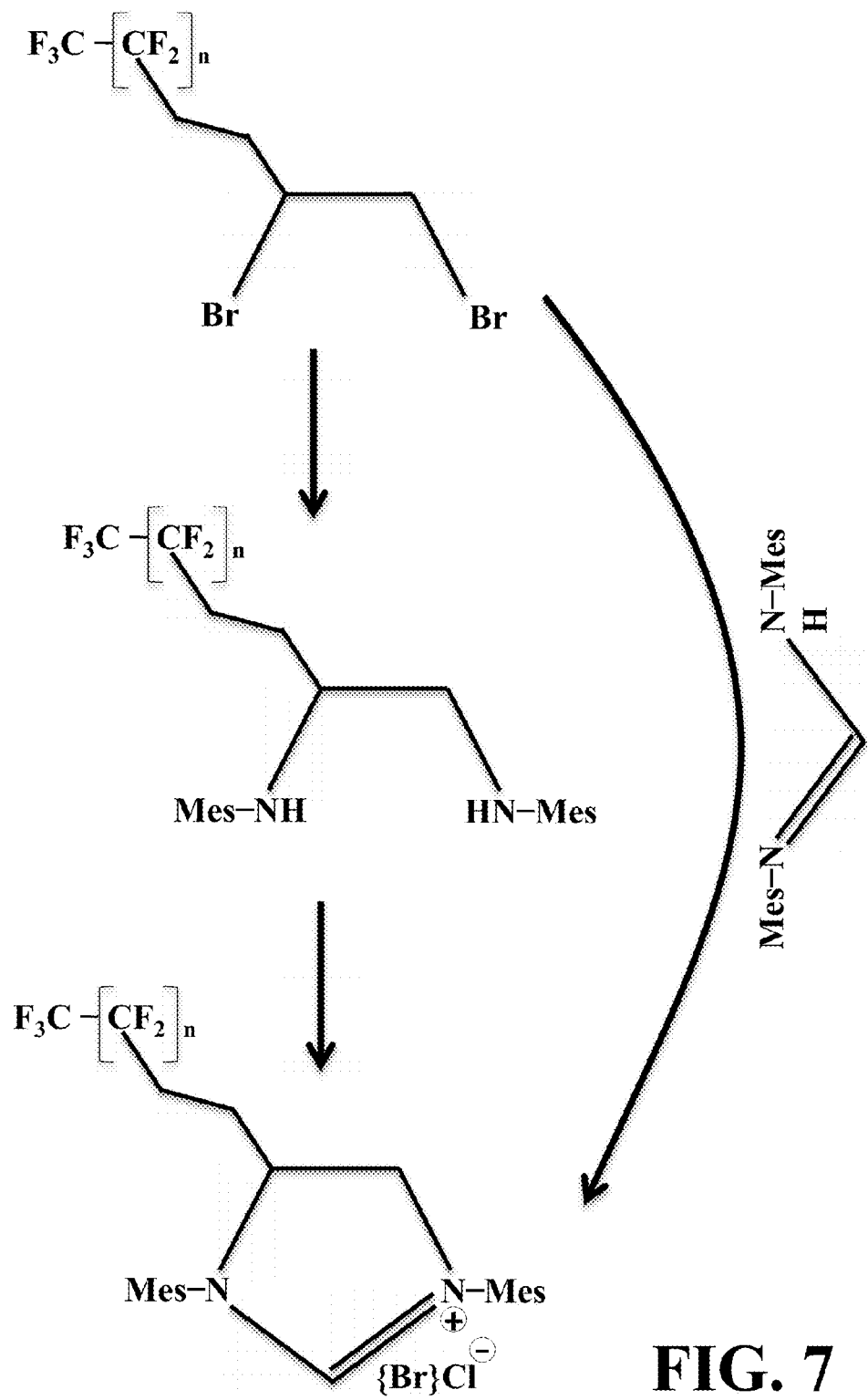
FIG. 7 is a schematic representation of a mechanism for synthesizing backfluorinated NHC carbenes with aromatic functionality according to another embodiment of the present invention.

With reference now to FIG. 7, a mechanism for synthesizing a backfluorinated NHC carbenes with aromatic functionality according to another embodiment of the present invention is described in detail. As shown, an arylamine/triethylamine mixture (for example, mesitylamine/triethylamine) is added to a tetrahydrofuran ("THF") solution of a perfluoroalkyl dibromide to form perfluoroalkyl dianiline. Addition of hydrogen chloride affords the hydrogen chloride salt of the dianiline. The salt may then be added to triethylorthoformate, and the mixture heated overnight. The reaction is cooled, and the product is isolated, washed, and dried to afford a white solid.

Backfluorinated NHC carbenes with aromatic functionality may alternatively be synthesized according to a method described in Kuhn et al., U.S. Application Publication No. 2011/0087032, entitled PREPARATION OF SATURATED IMIDAZOLINIUM SALTS AND RELATED COMPOUNDS, and published on Apr. 14, 2011. Briefly, as the skilled artisan having the benefit of this disclosure and Kuhn et al. would appreciate, the backfluorinated NHC carbenes with aromatic functionality may be synthesized by reacting equivalents of dimesityl formamidine, or one equivalent of dimesityl formamidine and one equivalent of diisopropylethylamine, with perfluoroalkyl dibromide. The mixture may be heated overnight to several days to form the backfluorinated NHC carbenes.

Backfluorinated NHC carbenes with aromatic or aliphatic functionality according to various embodiments of the present invention may be used in cold wall supercritical fluid deposition of noble metals onto complex substrates, such as bed plates, catalyst supports, nozzle throats, divert attitude control ("DAC") systems, and complex ducting. In that regard, and with reference now to FIG. 8, as well as reference again to FIG. 2, a method of depositing metals using supercritical fluid deposition methods is described in accordance with one embodiment of the present invention. In the case of noble metals, the purpose of the backfluorinated NHC carbene-metal complex is to render the metal precursor soluble in supercritical solvent, to render the metal precursor stable to hydrogen at lower temperatures, and to be removed and deposit the metal onto the substrate at elevated temperatures.

Figure 1:
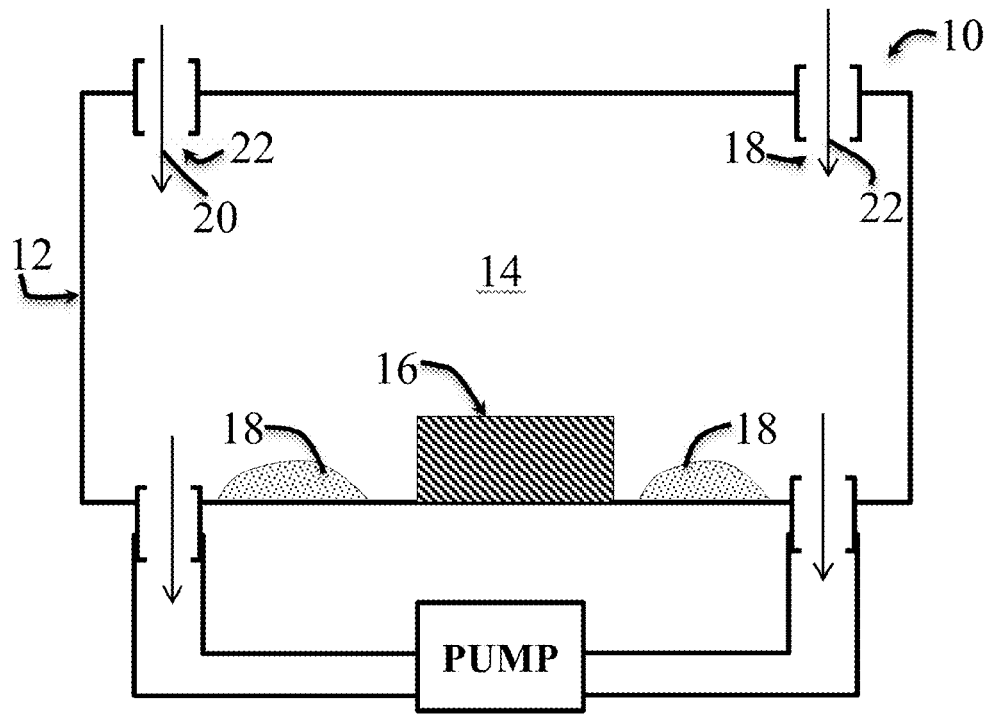
FIG. 1 is a schematic representation of a hot-wall processing system.
Figure 2:
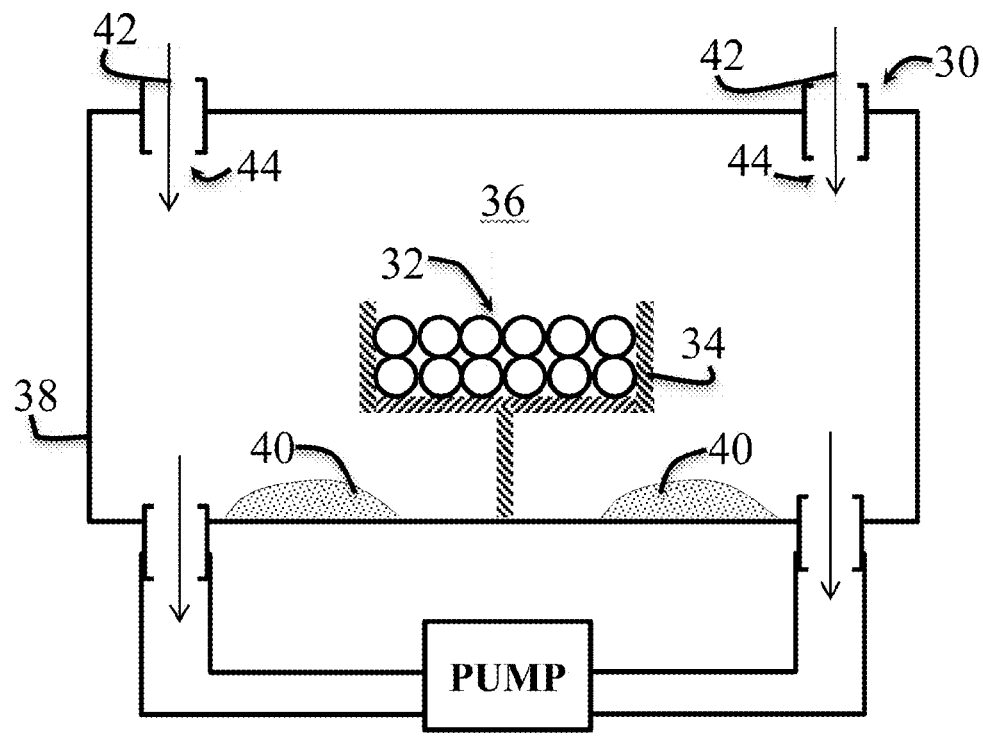
FIG. 2 is a schematic representation of a cold-wall processing system.
Figure 8:
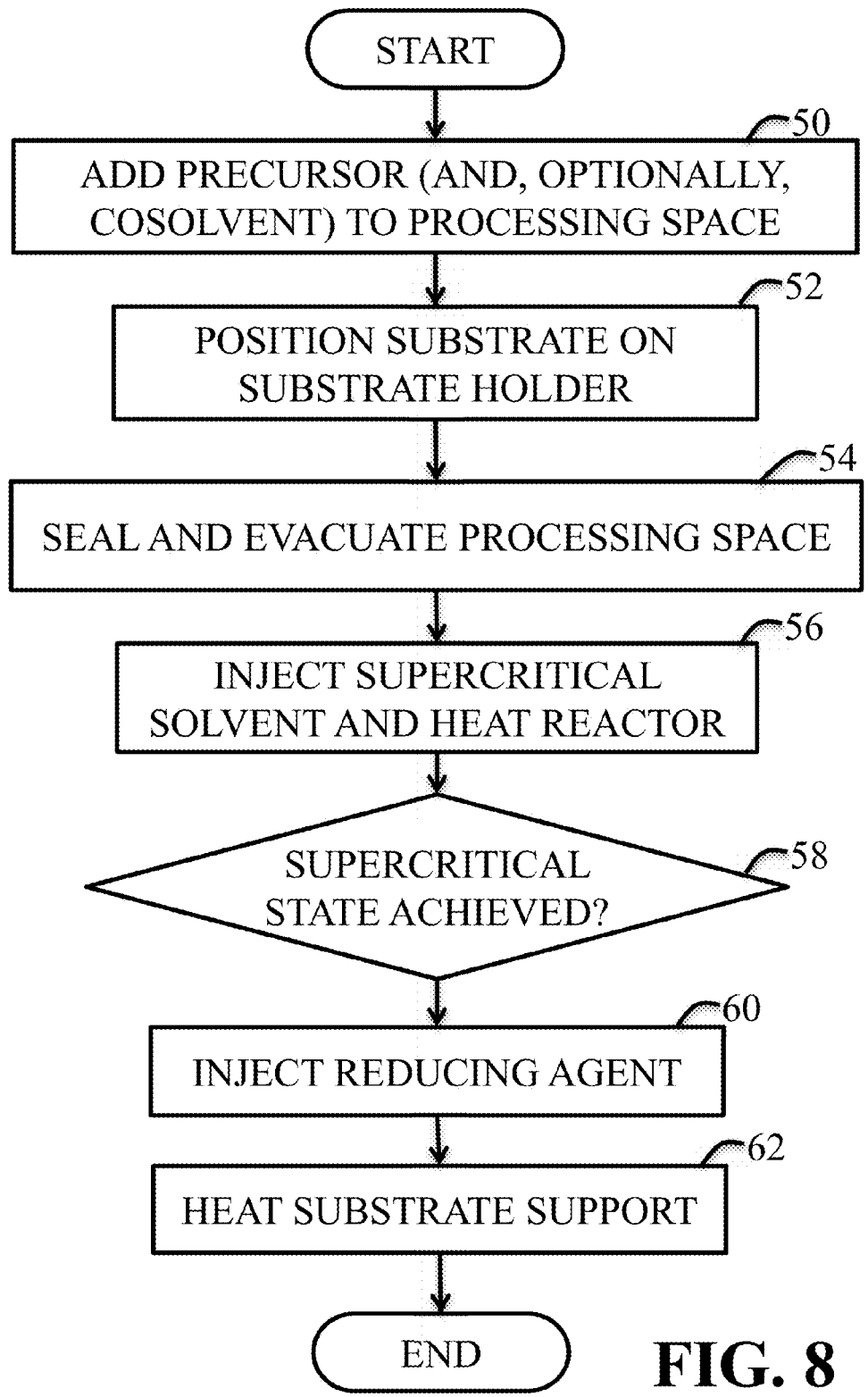
FIG. 8 is a flowchart illustrating a method of supercritical fluid deposition of metals using backfluorinated N-heterocyclic carbene-metal complexes according to an embodiment of the present invention.
Figure 9A:
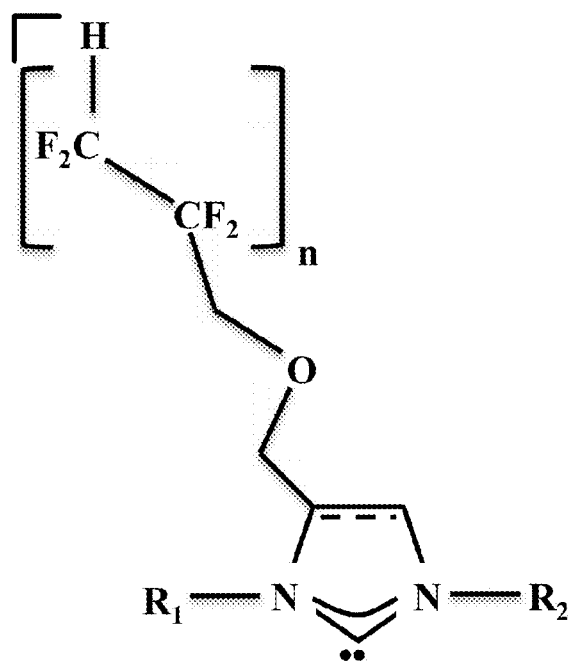
FIGS. 9A-9D are schematic representations of backfluorinated N-heterocyclic carbenes operable as ligands for a metal complex according to additional embodiments of the present invention.
Figure 9B:
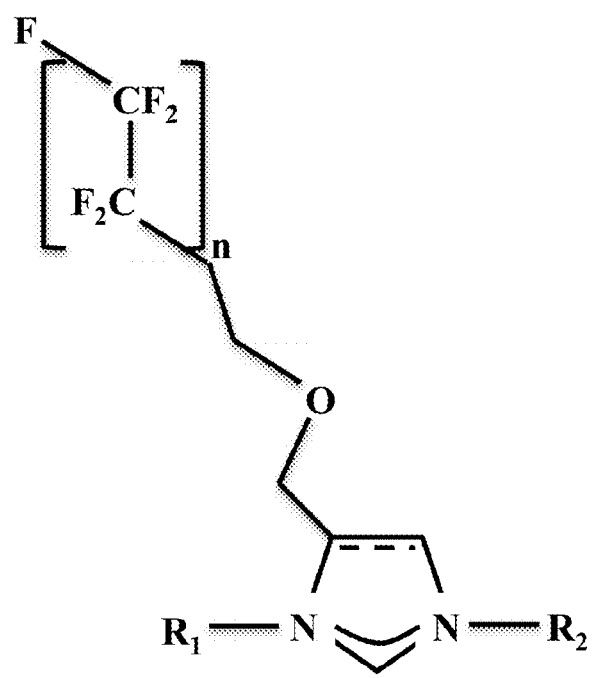
Figure 9C:
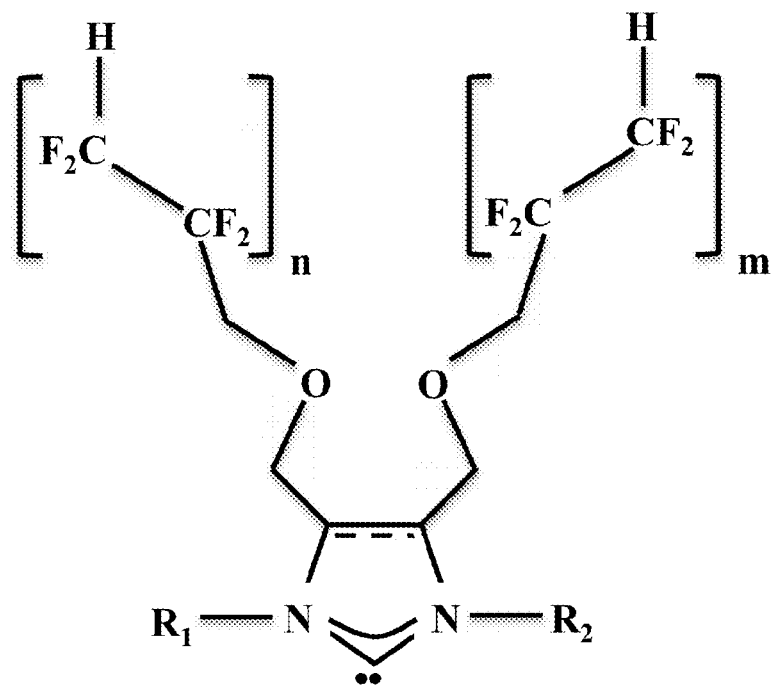
Figure 9D:
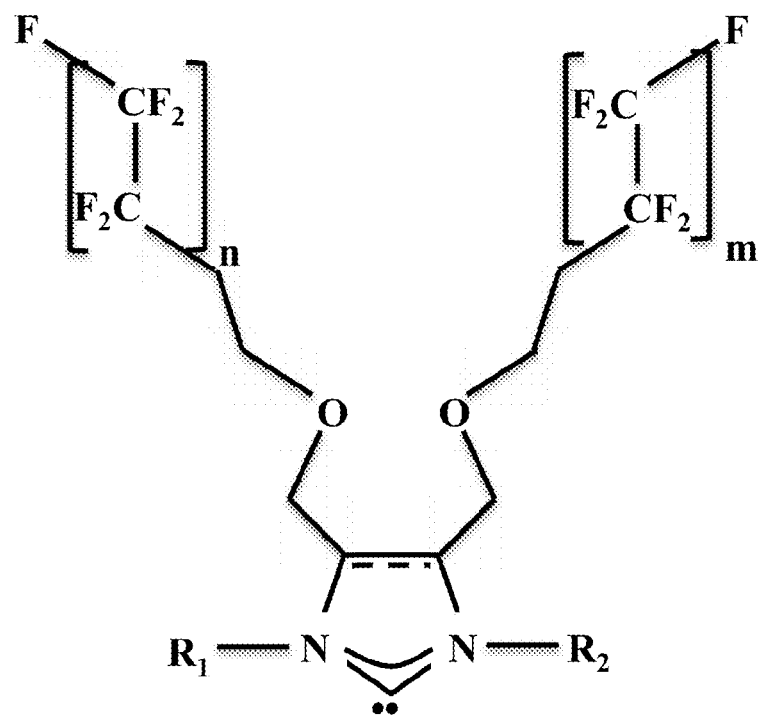

Using the cold-wall processing system 30 of FIG. 2, a noble metal may be deposited using SFD processing conditions according to an embodiment of the present invention illustrated in the flowchart of FIG. 8; however, the skilled artisan will readily appreciate that the illustrated cold wall reactor 30 layout should not be considered to be limiting. In the instant embodiment, the organometallic precursor 40 comprises a backfluorinated NHC carbene-metal complex according to at least one embodiment of the present invention.

In Block 50 of FIG. 8, a precursor 22 comprising a backfluorinated NHC carbene-metal complex, optionally with a cosolvent, is placed in the processing space 36. The substrate 32 is positioned on the substrate holder 34 (Block 52) and the processing space 36 is sealed and evacuated (Block 54).

A supercritical solvent, for example, carbon dioxide, may be injected via the injection system 44 and the chamber wall 38 may, optionally, be heated (Block 56). The reactor temperature depends on the selected supercritical solvent but, for exemplary purposes, may be 60° C. for carbon dioxide.

Once a supercritical state is achieved ("Yes" branch of Decision Block 58), the backfluorinated NHC carbene-metal complex precursor 40 begins to dissolve into the supercritical solvent, and a reducing agent may be injected via the injection system 44 (Block 60). Otherwise ("No branch of Decision Block 58), the injection (Block 56) continues.

With the backfluorinated NHC carbene-metal complex precursor 40 dissolved, the substrate holder 34 may be heated to a desired temperature (Block 62). Because the substrate holder 34, and ultimately the substrate 32 are at an elevated temperature, deposition of the metal portion of the backfluorinated NHC carbene-metal complex precursor 40 from the supercritical solvent onto the substrate 32 may occur without deposition of metal portion onto chamber walls 38 or other components of the system 30.

With deposition complete, the system 30 may be cooled, the pressure relieved, and the substrate 32 removed.

While not particularly shown herein, backfluorinated NHC carbenes and backfluorinated NHC carbene-metal complexes according to various embodiment of the present invention may be used within the field of catalysis. For example, backfluorinated NHC carbenes according to various embodiments of the present invention and as applied to transition metal catalyzed reactions afford new systems that are soluble in fluorinated solvents while retaining catalytic activity. More particularly, the disclosed backfluorinated NHC carbenes may be useful in biphase fluorous catalysis, wherein efficiency of a chemical reaction is increased by placing the active species in a fluorinated phase. Reactants, in a nonfluorinated phase, migrate into the fluorinated phase active species such that a chemical transformation takes place. The reactants may then migrate out of the fluorinated phase active species. Use of backfluorinated NHC carbene-metal complexes may increase efficient separation of product from the catalyst, particularly in system comprising fluorinated solvents or the reaction of olefins having a fluoroalkyl group.

According to other embodiments of the present invention, ligands (or at least first and second ligands, $L_1$ and $L_2$) of the inorganic backfluorinated may be selected from the group of molecules illustrated in FIGS. 9A-9D, wherein each of $R_1$ and $R_2$ may be hydrogen, $C_1$-$C_{20}$ alkyl, $C_2$-$C_{20}$ alkenyl, $C_2$-$C_{20}$ alkynyl, $C_2$-$C_{20}$ alkoxycarbonyl, $C_1$-$C_{20}$ carboxylate, $C_1$-$C_{20}$ alkoxy, $C_2$-$C_{20}$ alkenyloxy, $C_2$-$C_{20}$ alkynyloxy, an aryl, or an aryloxy; R' may be hydrogen, a fluorine, an aromatic ring, or combinations thereof; subscript m may range from 1 to 10; subscript n may range from 1 to 10; and subscript o may range from 0 to 3. If desired, $R_1$ and $R_2$ may further be substituted with fluorinated or partially fluorinated halogen, $C_1$-$C_5$ alkyl, $C_1$-$C_5$ alkoxy, $C_1$-$C_{20}$ alkyl, $C_1$-$C_{20}$ alkoxy, and a halogen substituted phenyl group.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. An N-heterocyclic carbene comprising a formula selected from the formulae consisting of:

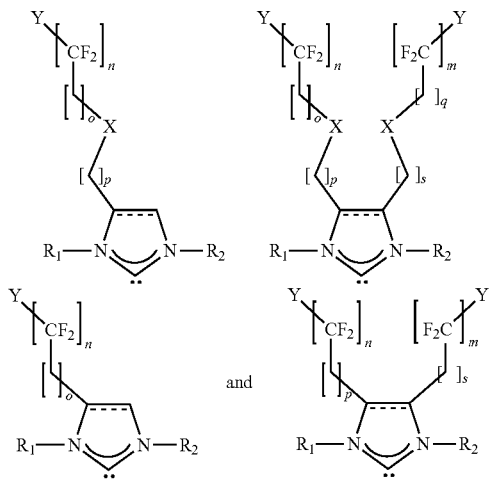

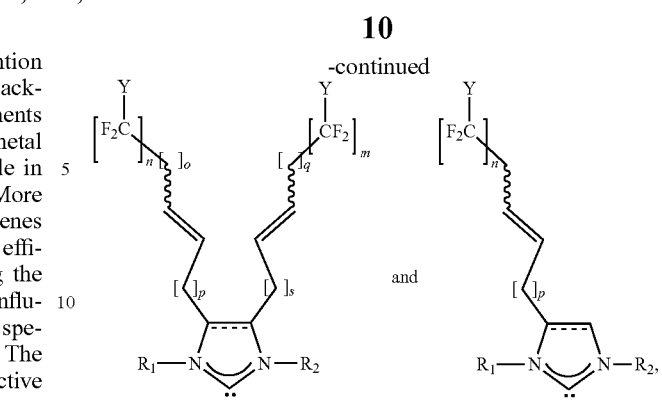

wherein X is oxygen, sulfur, nitrogen monohydride, or $SiR_2^1$, $R^1$ being an alkyl or an aryl;

Y is hydrogen, fluorine, an aromatic ring, or combinations thereof;

each of $R_1$ and $R_2$ is separately selected from a group consisting of hydrogen, a $C_1$-$C_{20}$ alkyl, a $C_2$-$C_{20}$ alkenyl, a $C_2$-$C_{20}$ alkynyl, a $C_2$-$C_{20}$ alkoxycarbonyl, a $C_1$-$C_{20}$ carboxylate, a $C_1$-$C_{20}$ alkoxy, a $C_2$-$C_{20}$ alkenyloxy, a $C_2$-$C_{20}$ alkynyloxy, an aryl, or an aryloxy;

the subscript m ranging from 2 to 20;

the subscript n ranging from 2 to 20; and each of the subscripts o, p, q, and s ranging from 0 to 3 and such that o+p+q+s>1.

2. An N-heterocyclic carbene-metal complex comprising: an inorganic metal complex; and at least one ligand selected from the N-heterocyclic carbene of claim 1.

3. The N-heterocyclic carbene-metal complex of claim 2, wherein the metal is selected from the group consisting of rhenium, ruthenium, osmium, rhodium, iridium, palladium, platinum, silver, gold, cobalt, nickel, palladium, platinum, and copper.

4. An N-heterocyclic carbene-metal complex having the formula:

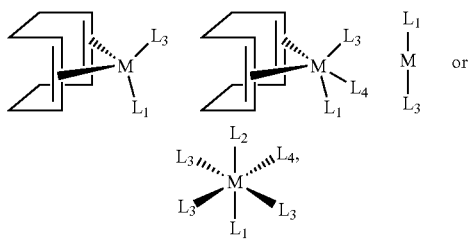

wherein at least one of $L_1$, $L_2$, $L_3$, and $L_4$ is selected from the N-heterocyclic carbenes of claim 2.

5. The N-heterocyclic carbene-metal complex of claim 4, wherein M is selected from the group consisting of rhenium, ruthenium, osmium, rhodium, iridium, palladium, platinum, silver, gold, cobalt, nickel, palladium, platinum, and copper.

6. The N-heterocyclic carbene of claim 1, wherein each of $R_1$ and $R_2$ is further substituted with a fluorinated or partially fluorinated group, $C_1$-$C_5$ alkyl, $C_1$-$C_5$ alkoxy, $C_1$-$C_{20}$ alkyl, $C_1$-$C_{20}$ alkoxy, and a halogen substituted phenyl group.

7. The N-heterocyclic carbene-metal complex of claim 4, wherein M is selected from the group consisting of rhenium, ruthenium, osmium, rhodium, iridium, palladium, platinum, silver, gold, cobalt, nickel, palladium, platinum, and copper.

8. A method of depositing a noble metal onto a substrate using a supercritical fluid deposition process in a cold wall reactor, the method comprising:

exposing the substrate to a supercritical solvent in a supercritical state;
dissolving the N-heterocyclic carbene-metal complex of claim 4 in the supercritical solvent, wherein M is the noble metal;
injecting a reducing agent into the supercritical solvent; and
heating the substrate such that a metal portion of the N-heterocyclic carbene-metal complex is deposited from the supercritical solvent onto the substrate.

9. The method of claim 8, wherein the noble metal is rhenium, ruthenium, osmium, rhodium, iridium, palladium, platinum, silver, or gold.

10. The method of claim 8, wherein the supercritical solvent is carbon dioxide and the reducing agent is hydrogen gas.

11. The method of claim 8, further comprising:
injecting a cosolvent while exposing the substrate to the supercritical solvent.

12. A method of depositing a noble metal onto a substrate using a supercritical fluid deposition process in a cold wall reactor, the method comprising:
exposing the substrate to a supercritical solvent in a supercritical state;
dissolving the N-heterocyclic carbene-metal complex of claim 4 in the supercritical solvent, wherein M is the noble metal;
injecting a reducing agent into the supercritical solvent; and
heating the substrate such that the N-heterocyclic carbene is deposited from the supercritical solvent onto the substrate.

13. The method of claim 12, wherein the noble metal is rhenium, ruthenium, osmium, rhodium, iridium, palladium, platinum, silver, or gold.

14. The method of claim 12, wherein the supercritical solvent is carbon dioxide and the reducing agent is hydrogen gas.

15. The method of claim 12, further comprising:
injecting a cosolvent while exposing the substrate to the supercritical solvent.

16. The metal complex of claim 4, wherein the N-heterocyclic carbene of the at least one of $L_1$, $L_2$, $L_3$, and $L_4$ is selected from the group consisting of:

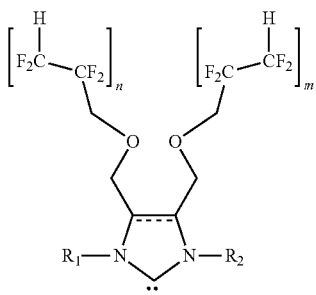

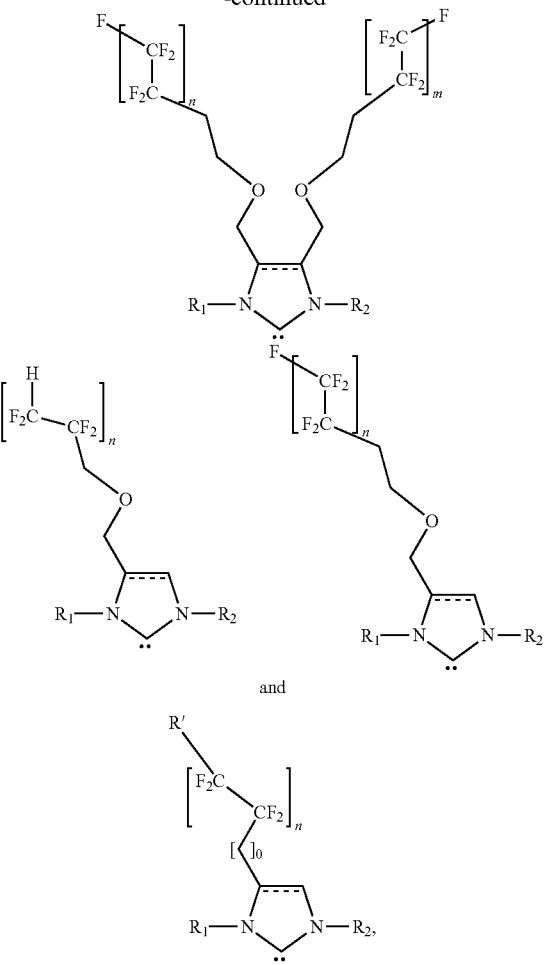

wherein R' is hydrogen, fluorine, an aromatic ring, or combinations thereof;

each of $R_1$ and $R_2$ is a hydrogen, a $C_1$-$C_{20}$ alkyl, a $C_2$-$C_{20}$ alkenyl, a $C_2$-$C_{20}$ alkynyl, a $C_2$-$C_{20}$ alkoxycarbonyl, a $C_1$-$C_{20}$ carboxylate, a $C_1$-$C_{20}$ alkoxy, a $C_2$-$C_{20}$ alkenyloxy, a $C_2$-$C_{20}$ alkynyloxy, an aryl, or an aryloxy;

the subscript m ranges from 1 to 10;

the subscript n ranges from 1 to 10;

and the subscript o ranges from 0 to 3.

17. The N-heterocyclic carbene of claim 1, with the proviso that the functionality of the selected $R_1$ and $R_2$ is not directly attached to the nitrogen.

18. The N-heterocyclic carbene of claim 1, wherein $R_1$ and $R_2$ are the same.

* * * * *